United States Patent [19]

Pieles et al.

[11] Patent Number: 5,112,963
[45] Date of Patent: May 12, 1992

[54] MODIFIED OLIGONUCLEOTIDES

[75] Inventors: Uwe Pieles; Uwe Englisch; Friedrich Cramer, all of Göttingen, Fed. Rep. of Germany

[73] Assignee: Max-Planck-Gesellschaft zur Foerderung der Wissenschaften e.V., Gottingen, Fed. Rep. of Germany

[21] Appl. No.: 270,243

[22] Filed: Nov. 14, 1988

[30] Foreign Application Priority Data

Nov. 12, 1987 [DE] Fed. Rep. of Germany ....... 3738460

[51] Int. Cl.$^5$ .................. C12Q 1/68; C07H 15/12
[52] U.S. Cl. ...................... 536/27; 536/28; 536/29; 435/6
[58] Field of Search .............. 536/27, 29; 435/6

[56] References Cited

U.S. PATENT DOCUMENTS

| 4,196,281 | 4/1980 | Hearst | 536/29 |
| 4,835,263 | 5/1989 | Nguyen et al. | |

FOREIGN PATENT DOCUMENTS

| 0117777 | 9/1984 | European Pat. Off. |
| 169787 | 1/1986 | European Pat. Off. |
| 214908 | 3/1987 | European Pat. Off. |
| 0266099 | 5/1988 | European Pat. Off. |
| 2540122 | 8/1984 | France |

OTHER PUBLICATIONS

Miller, Paul S. *Jerusalem Symp. Quantum Chem. Biochem.* 1985, "Control of gene expression by oligonucleotide methylphosphonate" pp. 207–219, abstr. in CA 104:220115x, 1985.

Isaacs, et al. (1982) "Trends in Photobiology" ed. C. Helene et al. Plenum Press, New York, pp. 279–294.
Bachellerie, J. P. et al. (1981) Nucl. Acids Res. 9:2207–2222.
Cazenave et al. (1989) Nucleic Acid Res. 17:4255–4271.
Louis J. Maher III and Bruce J. Dolnick (1988) Nuc. Acid Res. 16:3341–3358.

*Primary Examiner*—Robert A. Wax
*Assistant Examiner*—Frederick F. Tsung
*Attorney, Agent, or Firm*—Felfe & Lynch

[57] ABSTRACT

The present invention provides modified oligonucleotides, wherein, amongst the first four bases on the 5'-end, they have the base sequence AT or TA and, bound to one of the two O$^-$ groups of the 5'-phosphate group of the first nucleotide at the 5'-end of said oligonucleotide, they contain a radical of the general formula:

$$-R_4-O-CH_2 \quad \quad R_1 \quad \quad (I)$$

in which $R_4$ is a spacer group and $R_1$, $R_2$ and $R_3$ are hydrogen atoms or alkyl or alkoxy radicals containing up to 3 carbon atoms.

These modified oligonucleotides can be used for blocking the replication and/or expression of genes which have a sequence complementary with the modified oligonucleotides.

5 Claims, 2 Drawing Sheets

MODIFIED OLIGONUCLEOTIDES

The present invention is concerned with modified oligonucleotides, with the preparation thereof and also with the use thereof for blocking the replication and/or expression of genes.

Today, one of the great aims of biotechnical and medical research is to prevent the pathogenic expression of certain undesired gene products, the multiplication of viruses, as well as the multiplication of uncontrollably growing cell lines, such as is the case, for example, with cancers and psoriasis.

Thus, for combating malignant skin tumours of the so-called T-cell lymphoma type, it has been suggested in the New England Journal of Medicine, 316, p. 297, to remove malignant lymphocytes from the blood of the patient by cell separation processes, to treat with methoxypsoralen and thereafter to irradiate these lymphocytes with ultraviolet light. Psoralen and its derivatives are compounds intercalated between DNA double strands which, by the action of light on certain positions of the DNA, namely, on neighbouring opposite lying thymidine residues, are covalently coupled. In the above mentioned case, the DNA of the lymphocytes is permanently inactivated, whereafter they die off after a few days. However, directly after the extra-corporeal irradiation, the patient again receives the blood with the altered lymphocytes, whereby the damaged lymphocytes act somewhat like inoculants. The immune system of the body is activated and obviously directs itself against the still remaining T-lymphocytes, whereby the tumorous skin changes and the skin reddening regresses. The mechanisms by which these phenomena take place are still not clear and must be elucidated. Similar treatments have also been used for psoriasis.

This form of treatment is only possible today because subgroups of blood cells, such as malignant T-lymphocytes, can be isolated by separation processes, such as leukophoresis, and because extracorporeal devices are available in which pharmaceutical and irradiation can be allowed to act on these cells without acting on the entire organism. A disadvantage of this process, however is the non-specificity of the intercalation and coupling of the psoralen and of its derivatives in the total DNA of all treated cells at TA sequences and the necessity of separating diseased cells to be treated from healthy cells which are not to be killed off. The above process is only performable in special cases, as in the example mentioned above, as such this process can not be used, e.g., to inactivate virus-infected cells and thereby to stop the multiplication cf the virus or to prevent the expression of otherwise undesired cellular gene products, for example the oncogenic products of cancer cells.

A further method based on the same principle was suggested in U.S. Pat. No. 4,321,919. In this method, in order to reduce the lymphocyte count in the blood of patients with abnormally high lymphocyte levels, such as patients with lymphocytaemia, blood is taken from the patients and irradiated with ultraviolet light in the presence of psoralen. Subsequently the blood is again returned to the patient. The lymphocytes into the DNA of which psoralen is intercalated are destroyed via this treatment and the lymphocyte count is returned to a normal level via controlled use of the method. This method, however, does not allow one to differentiate between virus-infected cells and non-infected cells. This method involves a complete destruction of the cells but not on the elimination of expression of certain genes.

Psoralen and its derivatives according to European Patent Specification No. 0,184,331 are used in order to inactivate viruses, for example the HIV virus, in diagnostic test packs. Psoralen is added to a virus-containing supernatant, which is irradiated with the ultraviolet light followed by isolation of inactivated viruses therefrom. This reference does not provide a method for use of psoralen at a cellular level.

Therefore, it has been proposed in U.S. Pat. Nos. 4,693,981 and 4,545,987 to use a double-stranded viral RNA of the blue tongue virus (BTV, a double-stranded RNA virus), which has been inactivated by light-induced covalent coupling of psoralen, as inoculum against this virus. However, virus already present in a cell and integrated in a cellular DNA can not be specifically found and inactivated. On the contrary, such an inoculation can only be used as a prophylactic measure against infection with certain viruses.

It has already been attempted to direct psoralen to a specific site in plasmid DNA, for which purpose mercury-modified pyrimidines are incorporated into the plasmid pBR322 via nick translation (see Saffran et al., Proc. Natl. Acad. Sci. USA, 79, 4594-4558). The psoralen used was specifically bound in the dark by an Hg-S bond to this position and thereafter irradiated for the cross-linking of both strands. However, this method of specific coupling of psoralen to DNA can only be carried out with plasmids and the like in vitro since it is not possible to bring about such a modification in intact cellular DNA. Furthermore, in the case of this method, the nick translation with a restriction enzyme (Bam HI) is carried out together with ethidium bromide, which requires that a cleavage point for a restriction enzyme is present at the position to which the psoralen is to be coupled. Furthermore, this nick translation cannot be carried out quantitatively, because psoralen molecules only couple to about half of the DNA molecules involved.

Therefore, it is an object of the present invention to avoid the above-mentioned disadvantages and to provide compounds which make possible the introduction of a cross-linking, intercalating agent at a specific position in a gene in the intact cell and thus to prevent the expression of this gene or to bind a cross-linking agent onto already transcribed RNA and thereby to block the expression of the gene on the translation level.

Thus, according to the present invention, there are provided modified oligonucleotides, having either base sequence AT or TA among the first four bases on the 5' end, bound to one of the two O⁻ groups of the 5'-phosphate group of the first nucleotide at the 5'-end of said oligonucleotide, they contain a radical of the general formula:

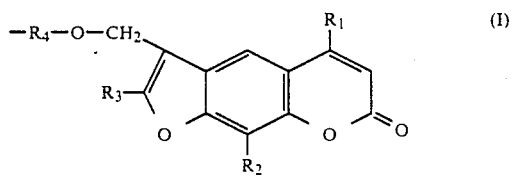

in which $R_4$ is a spacer group and $R_1$, $R_2$ and $R_3$ are hydrogen atoms or alkyl or alkoxy radicals containing up to 3 carbon atoms.

The modified oligonucleotides according to the present invention hybridize with single-stranded or double-stranded DNA or DNA complementary to them, the intercalated compound thereby being directed by the presence of the base sequence AT or TA on the oligonucleotide in the region of an $$\begin{array}{c} AT \\ TA \end{array}$$

base sequence in the double strand. In the case of double-stranded DNA, hybridization of the oligonucleotide takes place after partial breaking of the original double strand (C. Helene et al., Biochemie, 67, 777–783/1985) or by formation of a "triple helix" (T. Le Doan et al., Nucl. Acids Res., 15, 7749–7760/1987). After the intercalation of a radical of general formula (1) between the two hybrid nucleic acid strands (DNA/DNA or DNA/RNA), the strands, after irradiation with UV light, are cross-linked via covalent bonding of the two thymidine bases to the radical of the general formula (I).

In a preferred embodiment of the present invention, instead of the second $O^-$ group of the 5'-phosphate group and/or on one or more further phosphate groups of the oligonucleotide, the oligonucleotide carries a methyl radical or a thio group. It is thereby made possible for an oligonucleotide to penetrate through the cell membrane into a eukaryotic cell (Miller et al., Biochemie, 67, 769–776/1985; Marcus-Sekura et al., Nucl. Acids Res., 15, No.14, 5749 et seq./1987). However, for the solubility of the oligonucleotide, it is necessary that sufficient $O^-$ groups be maintained in order to ensure the solubility of the oligonucleotide. A general formula of the oligonucleotides according to the present invention is illustrated in FIG. 1 of the accompanying drawings.

In a further preferred embodiment of the present invention, the spacer group $R^4$ is a straight-chained or branched, substituted or unsubstituted alkylene or alkenylene radical, the spacer chain between the $O^-$ group of the 5'-phosphate and the oxygen atom in the 4'-side chain of the compound of general formula (II) thereby having a length of 2 to 4 carbon atoms. Especially preferably, the spacer group $R^4$ thereby has the general formula:

$$-(CH_2)_n$$

in which n is a whole number of from 2 to 6. The closer the intercalated compound after hybridization of the nucleic acid strand to the opposite-lying neighbouring thymidine bases, the greater the probability that the intercalation takes pace precisely at this position, which is essential for covalent cross-linking. A certain minimum length of the spacer is essential for the flexibility of the intercalated compound. Most preferably, the spacer group $R^4$ in the oligonucleotides according to the present invention is an ethylene radical. Furthermore, the first two bases of the oligonucleotide are preferably T and A.

In a further preferred embodiment of the present invention, modified oligonucleotides are used which, as radicals $R^1$, $R^2$ and $R^3$ are all methyl radicals and $R^4$ is an ethylene radical.

The length of the modified oligonucleotides is chosen in known manner (Szostak et al., Methods in Enzyml., 68, 419–428/1979) so that specific hybridization is possible at an appropriate temperature. This means that the shorter the oligonucleotide, the lower the temperature need be in order to cause hybridization with cellular or extracellular double-stranded or with single-stranded DNA. The chain length of the oligonucleotide is preferably 8 to 50 nucleotides.

The sequence of the oligonucleotides of the present invention is dependent upon the sequence of the gene to be hybridized therewith or of its mRNA. Such a gene can be any cellular or extracellular gene in which the oligonucleotide can be complementary not only to a part of the 5'-region of the gene, the initiator region of the expression region, to a part of the gene itself, to a part of the primary transcript or of the mRNA. The oligonucleotide is preferably complementary to a part of the gene such as a mutated gene, an oncogene or a gene essential for the multiplication of a virus.

The present invention also provides a process for the preparation of the modified oligonucleotides according to the present invention, wherein a compound the general formula:

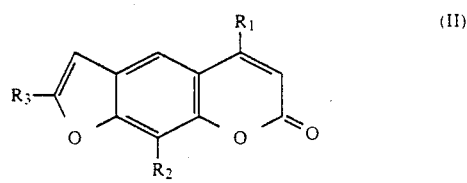

in which $R_1$, $R_2$ and $R_3$ are hydrogen atoms or alkyl or alkoxy radicals containing up to 3 carbon atoms, is reacted in known manner with chloromethyl ether and a dihydroxy straight-chained or branched, substituted or unsubstituted alcohol with the formation of a compound the general formula:

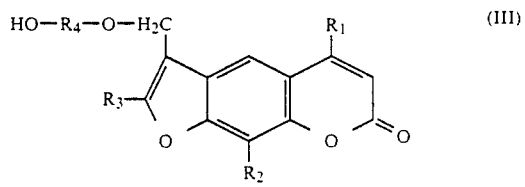

in which $R_1$, $R_2$ and $R_3$ have the above-given and $R_4$ is a spacer group, the compound (III) is reacted at ambient temperature with a compound to introduce a protected phosphite group, to give the resulting reaction product of the general formula:

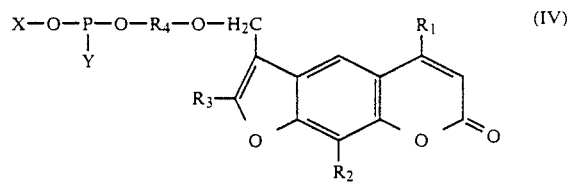

in which $R_1$, $R_2$ and $R_3$ and $R_4$ have the above-given meanings, X is a protective group and Y is a chlorine atom or an N,N-dimethylamino, N,N-diisopropylamine or morpholino radical, followed by condensation thereon, in a manner known for oligonucleotide synthesis, further nucleotides provided with a protective group in the desired sequence, the base sequence AT or TA being incorporated within the first four bases of the growing oligonucleotide chain, followed by oxidation and the removal of the protective groups from the resultant oligonucleotides.

In the process according to the present invention, the compound of general formula (II) is reacted with chloromethyl methyl ether, a chloromethyl radical thereby being bound to the 4'-position of the furan ring. In the case of reaction with the dihydroxy alcohol, this adds on to the chloromethyl radical with the splitting off of hydrogen chloride, which results in the formation of the compound of general formula (III). These two reactions are described in U.S. Pat. No. 4,269,852.

After introduction of the protected phosphite groups has taken place, the compound of general formula (IV) is then used as starting compound for the oligonucleotide synthesis. The phosphite group preferably carries an N,N-diisopropylamino radical bound to the phosphorus atom and a protective group bound to an oxygen atom thereof, such as is also used as a protective group in the case of the oligonucleotide synthesis The oligonucleotide synthesis is carried out according to known methods, for example as described by Caruthers et al., Science, 230, 281–285/1980.

Since, as already mentioned, for the specificity of the incorporation of the intercalating compound into the DNA double strand, it is important that the base sequence
is present as closely neighbouring as possible to the intercalating group, within the first four bases of the growing nucleotide chain there is incorporated the base sequence AT or TA. The further base sequence of the modified oligonucleotide is so chosen that it is complementary to a part of a gene, the expression of which is to be blocked, or to its mRNA. After the condensing on of the desired oligonucleotide synthesis, the phosphite groups are oxidised to phosphate groups and the protective groups still present on the phosphate groups removed by hydrolysis.

Monochloro-($\beta$-cyanoethyl-N,N-diisopropylamino) phosphite is preferably used as a compound for transferring a protected phosphite group, oxidation being carried out with $I_2$/water/lutidine or $S_8$/$CS_2$/pyridine. Oligonucleotides are thereby prepared which received on the phosphate atom of the 5'-phosphate group and possibly on further phosphate groups within the oligonucleotide chain, depending upon the nature of the oxidation during the oligonucleotide synthesis, a negatively charged oxygen atom and/or a negatively charged sulphur atom and a double-bound oxygen atom. Furthermore, in the case of carrying out the oxidation with $S_8$/$CS_2$/pyridine, oligonucleotides can also be obtained which, on one or more phosphate groups, contain a double-bound sulphur atom instead of the double-bound oxygen atom. The introduction of the protected phosphite group takes place in the manner described by Singha et al., Nucl. Acids Res., 12, 4539/1984.

In a further preferred embodiment of the present invention, as a compound introducing a protected phosphite group there is preferably used monochloro($\beta$-methyl-N,N-diisopropylamino) phosphite and/or possibly several nucleoside methyl phosphonamidites for the oligonucleotide synthesis, oxidation being carried out with $I_2$/water/lutidine. There are thereby prepared mixed oligonucleotides in the case of which the nucleosides are bound partly by phosphate residues and partly by methyl phosphonate residues. Oligonucleotide methyl phosphonates or phosphorothioates are resistant to nuclease decomposition and can pass the membranes of mammalian cells (Miller et al., Biochemie, 67, 769–776/1985; Marcus-Sekura et al., Nuc. Acids Res., 15, No. 14, 5749 et seq./1987). The hybridisation behaviour to complementary nucleic acid sequences of cellular DNA or RNA is not impaired in the case of such oligonucleotide methyl phosphonates or phosphothioates. However, in the case of pure oligonucleotide methyl phosphonates, their use is limited due to their poor water solubility above a chain length of 8 to 10 nucleotides, for which reason, in the oligonucleotides according to the present invention, the nucleosides are bound by normal phosphate groups and methyl phosphonates and/or phosphothioate groups.

As dihydroxy alcohol, according to the present invention there is preferably used a straight-chained or branched, substituted or unsubstituted alkanediol or alkenediol.

Especially preferred is an alkanediol of the general formula HO-$(CH_2)_n$-OH, in which n is a whole number of from 2 to 4. Most preferably, ethylene glycol is used as alkanediol. In the compounds of general formulae (III) and (IV), the spacer group $R^4$ thereby preferably has the meaning $-CH_2-CH_2-$.

In a further preferred embodiment of the present invention, there is preferably used a compound of general formula (II) in which the radicals $R^1$, $R^2$ and $R^3$ are each methyl radicals and the dihydroxyl alcohol is ethylene glycol. The compound of general formula (II) with this meaning of the radicals $R^1$ $R^3$ is 4,5',8-trimethylpsoralen.

For a preferred embodiment of the present invention, the preparation of the modified oligonucleotides is illustrated schematically in FIG. 2 of the accompanying drawings.

In order to couple the intercalating compound of general formula (II) close to the base pair TA in the oligonucleotide, in the oligonucleotide synthesis, there is first condensed on to the compound of general formula (IV) a thymidine monophosphate and then an adenosine monophosphate, in each case in the protected form used for the oligonucleotide synthesis.

The present invention is also concerned with the use of modified oligonucleotides such as are described above for blocking the expression of genes which have a sequence complementary with the modified oligonucleotide.

For this purpose, the modified oligonucleotide is introduced into the target cells which contain this gene and the cells are irradiated with ultra-violet light.

By the use of the modified oligonucleotides according to the present invention, it is possible specifically to block particular genes, the sequence of which is, at least in part, known. By hybridisation of the complementary oligonucleotide with either the DNA sequence of the gene to be blocked, with the primary transcript or the mRNA (in the case of double-stranded DNA after partial breaking of the double strand), a hybrid double strand is formed and the intercalating compound coupled to the oligonucleotide is introduced close to the 5'-region of the hybrid strand between the nucleic acid strands. The modified oligonucleotide is thereby complementary to a region of the corresponding gene or to the mRNA in which the bases T and A occur neighbouring at least once. Since the modified oligonucleotide contains these two bases in the complementary base sequence, due to the hybridisation, the intercalating compound is brought into the region of such a base sequence and intercalates in this region and then, by irradiation at 360 nm, the two DNA strands are covalently bound via the neighbouring opposite-lying thymidine residues. Due to this covalent binding, it is now no longer possible that a primary transcript is formed and therefrom an mRNA for the transcription of the corresponding gene or the primary transcript is processed to mRNA or mRNA is translated into a protein.

In the case of the blocking of the expression according to the present invention of genes, the part of the gene to be blocked, to which the modified oligonucleotide is complementary, can be not only the 5'-region of the gene but also the initiation position of the gene, a part of the gene itself or the transcript. By binding on the 5'-region of the gene and covalent cross-linking of the two hybrid DNA strands in this region, the promotor action, as well as also the action of further elements of the upstream region of a gene important for the transcription, is destroyed. By cross-linking of the hybrid DNA strands in the region of the initiation positions, the action of RNA polymerase for the build up of a primary transcript is prevented. By cross-linking of the hybrid DNA within the gene, there is brought about the break off of the primary transcript formed at this position. An intact mRNA and thus an intact gene product can thereby also not be formed.

Furthermore, according to the present invention, it is also possible to prevent already transcribed primary transcripts or mRNA being translated into the corresponding proteins. However, since the gene is not blocked and the cells can continuously form further mRNA, for this purpose it is necessary to supply to the cells continuously the modified oligonuceotide for the compensation of the primary transcript or of the mRNA.

The use according to the present invention of the modified oligonucleotides for blocking the expression of genes can be carried out not only in eukaryotes but also in prokaryotes. In prokaryotes there is thereby also possible the blocking of the expression of sequences lying on extrachromosomal DNA or RNA (plasmid, cosmid, double-stranded or single-stranded DNA phages and RNA phages).

However, the blocking according to the present invention of the expression of genes is preferably carried out in eukaryote cells in which, in a preferred embodiment of the present invention, the target cells are virus-infected cells and modified oligonucleotides are used which are complementary to a part of a gene essential for the virus multiplication. It is thereby also possible to make harmless viruses which introduce their genom into the cellular DNA where it is then latently present in order to begin the virus production at a particular moment. The prerequisite for this is, naturally, that at least a part sequence of the corresponding virus is known, which is the case for most viruses. The blocking of cellular or viral oncogenes introduced into the cells is also possible in this way. It is thereby conceivable to treat some types of cancer, the cause of which is due to certain retroviruses. The only prerequisite for this is that, after administration of the modified oligonucleotides, the target cells can be irradiated with UV light. In the case of humans and animals, this is preferably carried out extracorporeally.

In the case of a preferred embodiment of the present invention, for blocking the gene expression of mammalian cells, there is used a modified oligonuceotide which is substituted on at east one and at most on all apart from one phosphate group by a methyl radical and/or thio group. As already mentioned above, such modified oligonucleotides can pass the cell membrane and thus get into the interior of the cell.

The extracorporeal irradiation of cells is, naturally, especially easy to carry out in the case of cells which are present in humand blood since, thanks to modern apparatus and medical methods of treatment, it is possible to remove part of the blood and to reintroduce it into the body after treatment has taken place. Therefore, according to a preferred embodiment of the present invention, for the treatment of a virus-infected leukocyte fraction in the case of humans and animals with oligonucleotides according to the present invention, after administration of the oligonucleotide, blood is removed, extracorporeally irradiated and then again introduced into the body.

According to a further preferred embodiment of the present invention, for the treatment of HIV-infected lymphocytes, oligonucleotides are used which are complementary to a part of the reverse transcriptase gene of the HIV virus and the blood of the patients is extracorporeally irradiated in several cycles after each partial removal and thereafter again introduced into the body. The viral reverse transcriptase gene is thereby blocked in the infected lymphocytes so that a conversion of the DNA of the provirus integrated in the cells into viral RNA is no longer possible and, consequently, the multiplication cycle of the virus is blocked. Therefore, virus multiplication can no longer result from such a cell which prevents the infection of further lymphocytes, in this case the T4 cells. The virus would thereby be made harmless although its genom still remains integrated in the cellular genom. Because of the present complete absence of methods for the treatment of Aids, this preferred use of the present invention is an important step for combating the disease since already infected patients can be cured. Thus, all opportunistic appearances of diseases which can arise due to destruction of the T4 cells do not occur.

Because of the potential toxicity of the intercalating compounds, in a further preferred embodiment the modified oligonucleotide is not administered orally or by injection into the patient but blood already removed is treated with the modified oligonucleotide and then irradiated extracorporeally, all possible harmful effects of the modified oligonucleotide on the human and animal organism hereby being avoided.

By means of the modified oligonucleotides according to the present invention and their use for blocking the expression of genes, it is thus possible to block specifically the expression of particular undesired gene products in the human and animal body. For this purpose, there is needed neither a manipulation of the chromosomal DNA nor are other unaffected genes impaired as is the case with a non-specific treatment with intercalating agents. Therefore, the modified oligonucleotides according to the present invention and the use thereof represent a great advance in the medical treatment of virus diseases and of inborn and genetically developed defects, for example cancer and psoriasis.

The following Examples are given for the purpose of illustrating the present invention, reference thereby being made to the accompanying drawings, in which.

EXAMPLE 1

Figure 1:
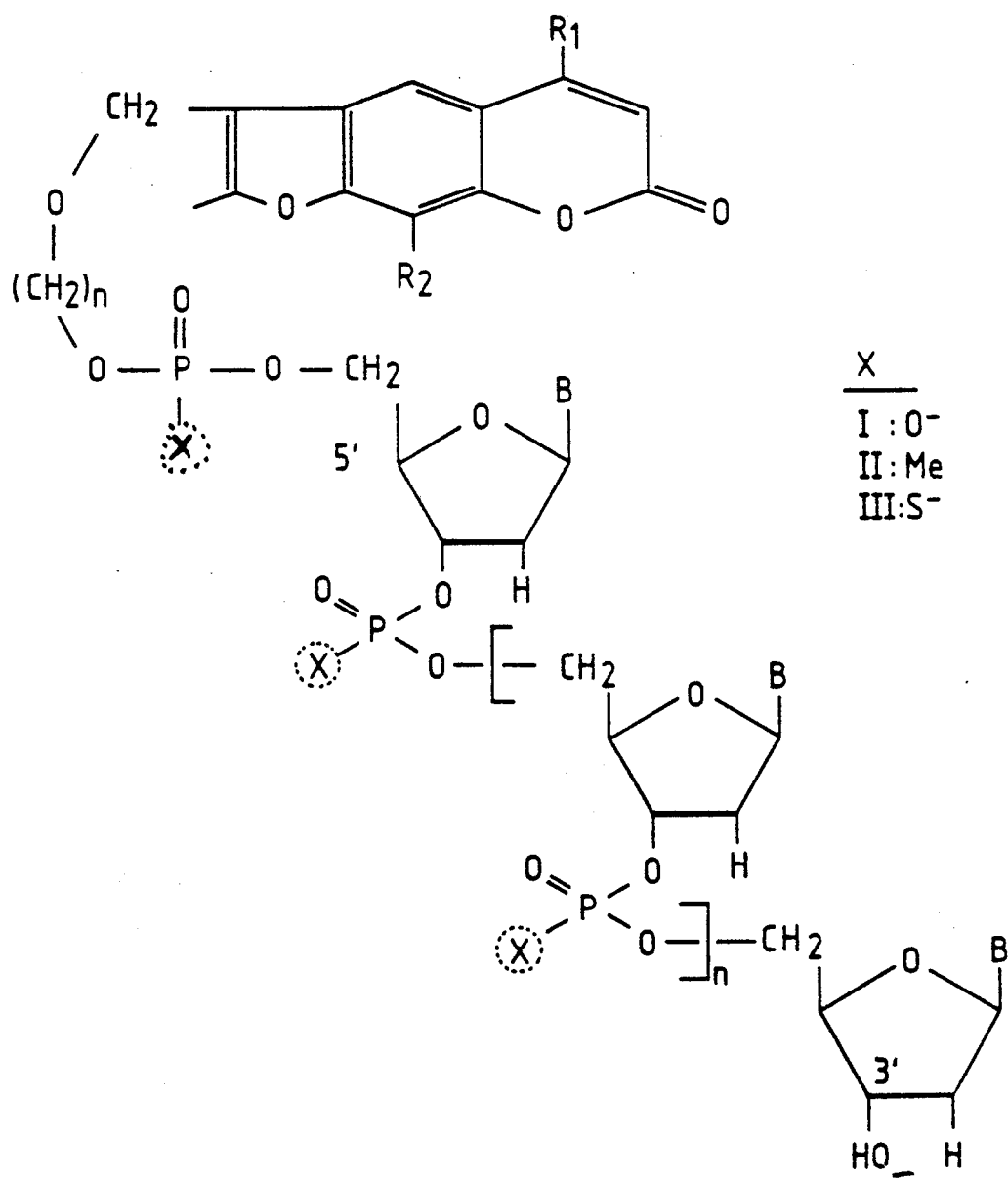
FIG. 1 is an oligonucleotide modified according to the present invention.
Figure 2:
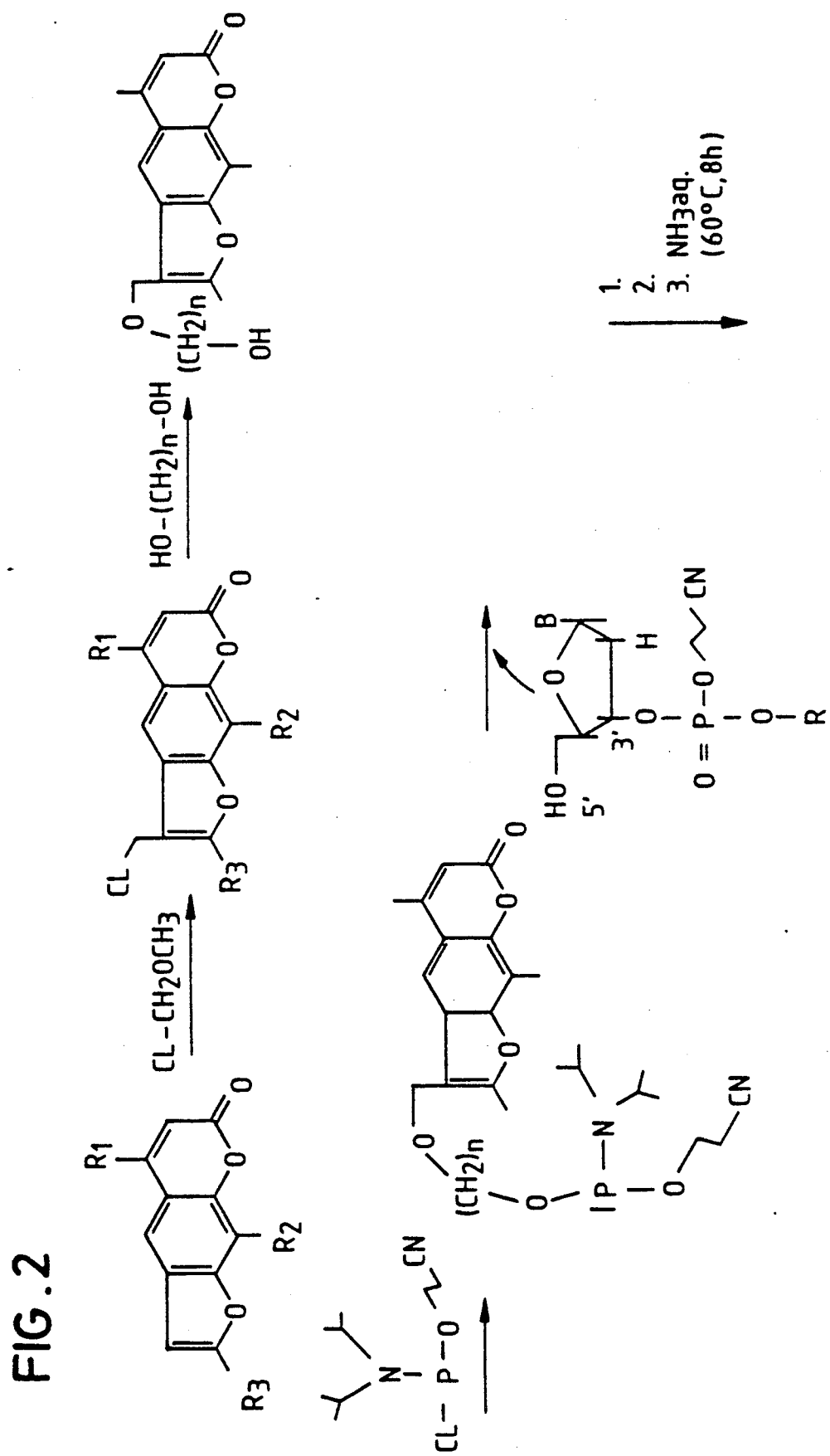
FIG. 2 is a schematic representation of a preferred process for the preparation of modified oligonucleotides.

Preparation of a modified oligonucleotide a) 1.38 g. (5.74 mMole) 4,5',8-Trimethylpsoralen is dissolved in 120 ml. glacial acetic acid with gentle warming. After cooling to ambient temperature, 10 ml. (131.6 mMole) chloromethyl methyl ether are added thereto and the reaction mixture is stirred for 24 hours at ambient temperature with the exclusion of light. After 24 hours, a further 10 ml. chloromethyl methyl ether are added thereto and stirring is continued for a further 24 hours. The reaction mixture is then placed on ice for 12 hours, whereafter the precipitate obtained is filtered off with suction and dried in a high vacuum at 40° C. Yield 1.05 g. (63.0% of theory). $^1$H-NMR (CDCl$_3$) TMS=2.6-2.7 (9H, m, C4.5',8-methyl), 4.8 (2H, s, CH$_2$Cl), 6.3 (1H, s, C3-H), 7.6 (aH, s, C5-H).

b) 360 mg. (1.3 mMole) 4-Chloromethyl-4,5',8-trimethyl-psoralen are then suspended in 8 ml. ethylenediol, whereafter the mixture is heated to 100° C. until the psoralen derivative is completely dissolved. Stirring is continued for 10 minutes at the given temperature. After cooling, the reaction mixture is diluted with 10 ml. water and extracted three times with, in each case, 5 ml. dichloromethane. The combined organic phases are dried over anhydrous sodium sulphate and, after filtration, evaporated to dryness. Purification of the crude product takes place on silica gel. As elution agent, there is used dichloromethane/methanol with an increasing content of methanol in 0.5% steps. However, a sufficient purity can also be achieved by recrystallisation from acetonitrile. The yield is 310 mg. (78% of theory). The compound obtained was identified via $^1$H-NMR spectroscopy. $^1$H-NMR (CDCl$_3$) TMS: 2.5 ppm (s. 6H, —CH$_3$), 2.57 (s, 3H, —CH$_3$), 3.6 to 3.84 (m, 4H, ethylene), 6.26 (s, m, 1H, pyrone), 7.6 (s, 1H aromat.).

c) 360 mg. (1.19 mMole) of this compound are dissolved in 10 ml. dichloromethane and mixed with 424 mg. (3 mMole) diisopropylethylamine, with the exclusion of moisture. 310 mg. (1.31 mMole) monochloro-($\beta$-cyanoethyl-N,N-diisopropylamino) phosphite are now slowly added dropwise thereto. The reaction mixture is then stirred at ambient temperature for 30 minutes. After conclusion of the reaction (thin layer chromatography), it is stopped by the addition of 5 ml. of a semisaturated aqueous solution of sodium hydrogen carbonate. The dichloromethane phase is washed twice with semisaturated aqueous sodium hydrogen carbonate solution and finally dried over anhydrous sodium sulphate. The product obtained by evaporation of the organic phase is purified on silica gel. As elution agents, there are used:

1. dichloromethane/diethylamine 10:1 v/v
2. n-hexane/triethylamine 10:1 v/v.

Solutions 1 and 2 are mixed in the ratio of 1:1. The yield is 419 mg. (85% of theory). The compound is analysed by $^{31}$P spectroscopy.

$^{31}$P-NMR (CDCl$_3$) H$_3$PO$_4$=S 149.54 ppm.

d) The coupling of the psoralen phosphoamidide thus obtained to further nucleotides takes place according to standard conditions of oligonucleotide synthesis according to the solid phase phosphoamidide method of Caruthers (Science, 230, 281–285/1985).

Run-off diagram of the oligonucleotide synthesis using the example of the sequence complementary to the start sequence of the Lac Z gene from M13 mp19: 3'AGT GTG TCC TTT GTC GAT X ; X=psoralen derivative The psoralen derivative is used under the same conditions as a normal nucleotide.

synthesiser: model Sam One of the firm Biosearch phosphoramidite nucleotide.

Per coupling, 40 to 45 mg. of the particular phosphoramidite nucleoside are dissolved in 700 $\mu$l. dry acetonitrile and 24 mg, tetrazole, also dissolved in 700 $\mu$l. of dry acetonitrile, are added thereto.

As solid phase, there are used 50 mg. of controlled pore glass resin of the firm Pierce which had been derivatised according to the procedure of M. J. Gait, Oligonucleotide Synthesis, a practical approach. pub. IRL Press (1984), p. 45 et seq., with the appropriate starting nucleosides, here A.

Typical synthesis protocoll using the example of the first coupling:

| | | |
|---|---|---|
| wash A | acetonitrile | 1:00 min. |
| capping | acetic anhydride 7.5 ml. lutidine 7.5 ml. N-methylimidazole 1.7 ml. in 40 ml. tetrahydrofuran | 1:00 min. |
| wash A | acetonitrile | 1:00 min. |
| deblock | splitting off of the 5'-protective group 3% dichloroacetic acid in dichloroethane | 1:25 min. |
| wash A | acetonitrile | 1:00 min. |
| wash B | acetonitrile | 1:00 min. |
| couple | nucleotide is mixed with catalyst | 0:32 min. |
| mix | coupling | 1:30 min. |
| wash A | acetonitrile | 0:30 min. |
| wash B | acetonitrile | 0:30 min. |
| oxidation | 1.5 g. iodine in 50 ml. tetrahydrofuran. 5 ml. water and 5 ml. lutidine | 0:45 min. |

EXAMPLE 2

Hybridisation of the psoralen-modified oligonucleotide with the start sequence of the Lac Z gene of single-strand bacteriophage DNA M13 mp19.

50 ng. of the ss-DNA of the bacteriophage are hybridised with 150 ng. of the modified oligonucleotide in a volume of 100 $\mu$l. For this purpose, the sample is heated for 10 minutes to 70° C., and subsequently allowed to cool for 30 to 40 minutes at 37° C. in a hot block. Seven samples treated in this manner are now irradiated with light with a wavelength of 360 nm, irradiation being carried out for 0, 1, 3, 5, 10, 20 and 30 minutes. 10 $\mu$l. of a particular sample are used for the transformation of competent cells (calcium chloride method). *Escherichia coli* cells of the strain JM 101 are used.

For the transformation, the 10 $\mu$l. of sample are mixed with 300 $\mu$l. of competent cells and left to stand on ice for 30 minutes. During this time, a solution is prepared of 3 ml. fresh cells (OD$_{600}$=0,6) and, in each case, 10 mg. 5-bromo-4-chloro-3-indolyl-$\beta$-D-galactopyranoside in 500 $\mu$l. dimethylformamide and 10 mg, isopropyl-$\beta$-D-thiogalactopyranoside in 500 $\mu$l. water.

280 $\mu$l. of each of these are added to the transformation batches, the whole sample is then added to 3 ml. of H-top agar with a temperature of 42° C. and subsequently pated out on to H plates, followed by incubation for 18 to 20 hours at 37° C.

In the case of all samples treated in this manner, there is observed the widest possible absence of the blue coloration of the plaque typical for the normal galactosidase reaction, as well as a drastic reduction of the plaque count in comparison with a non-irradiated sample which has not been hybridised with the modified oligonucleotide.

We claim:

1. A modified oligonucleotide characterized by having a base sequence AT or TA among the first two bases on its 5'-end and further characterized by having bound to one of the O⁻ radicals of the 5'-phosphate group of the first nucleotide at the 5'end of said oligonucleotide a moiety of the formula:

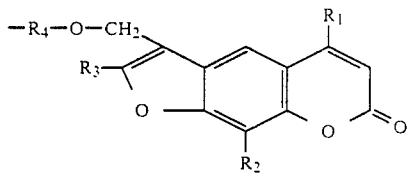

wherein $R_4$ is an ethylene spacer group and $R_1$, $R_2$, and $R_3$, which may be the same or different are hydrogen or $C_1$-$C_3$ alkyl or $C_1$-$C_3$ alkoxy with the proviso that not every phosphate moiety of said oligonucleotide is substituted by a methyl group.

2. Modified oligonucleotide of claim 1 wherein at least one O⁻ radical of said oligonucleotide of replaced by an S⁻ radical.

3. Modified oligonucleotide of claim 1, wherein the oligonucleotide has a chain length of 8 to 50 nucleotides.

4. Modified oligonucleotide of claim 1, wherein $R_1$, $R_2$ and $R_3$ are methyl radicals.

5. Oligonucleotide of claim 1 wherein said oligonucleotide is complimentary to the sequence of the target nucleic acid.

* * * * *